US008639335B2

(12) United States Patent
Peichel et al.

(10) Patent No.: US 8,639,335 B2
(45) Date of Patent: Jan. 28, 2014

(54) DISABLING AN IMPLANTED MEDICAL DEVICE WITH ANOTHER MEDICAL DEVICE (75) Inventors: David J. Peichel, Minneapolis, MN (US); Wing Kam Li, Minneapolis, MN (US); Gregory A. Haider, St. Paul, MN (US); David P. Dvorak, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 281 days.

(21) Appl. No.: 13/090,780

(22) Filed: Apr. 20, 2011

(65) Prior Publication Data
US 2012/0197332 A1   Aug. 2, 2012

Related U.S. Application Data (60) Provisional application No. 61/437,460, filed on Jan. 28, 2011.

(51) Int. Cl.
*A61N 1/37* (2006.01)

(52) U.S. Cl.
USPC .................................. 607/27; 607/2; 607/16

(58) Field of Classification Search
None
See application file for complete search history.

(56) References Cited

U.S. PATENT DOCUMENTS

| 4,313,441 | A  | 2/1982  | Buffet |
| 4,543,955 | A  | 10/1985 | Schroeppel |
| 4,787,389 | A  | 11/1988 | Tarjan |
| 4,987,897 | A  | 1/1991  | Funke |
| 5,617,871 | A  | 4/1997  | Burrows |
| 6,704,602 | B2 | 3/2004  | Berg et al. |
| 6,839,596 | B2 * | 1/2005 | Nelson et al. ............. 607/59 |
| 7,512,448 | B2 | 3/2009  | Malick et al. |
| 7,548,787 | B2 | 6/2009  | Feher |
| 7,630,767 | B1 | 12/2009 | Poore et al. |
| 7,634,313 | B1 | 12/2009 | Kroll et al. |
| 7,713,195 | B2 | 5/2010  | Zdeblick |
| 7,782,190 | B1 * | 8/2010 | Martin et al. ............. 340/539.12 |
| 7,945,333 | B2 * | 5/2011 | Jacobson .................. 607/59 |
| 8,295,939 | B2 * | 10/2012 | Jacobson ................. 607/59 |
| 8,352,025 | B2 * | 1/2013 | Jacobson .................. 607/2 |
| 2001/0031997 | A1 | 10/2001 | Lee |
| 2002/0045920 | A1 | 4/2002 | Thompson |
| 2003/0212441 | A1 | 11/2003 | Starkweather et al. |
| 2004/0225338 | A1 | 11/2004 | Lebel et al. |
| 2006/0095079 | A1 | 5/2006 | Gerber |
| 2006/0241705 | A1 | 10/2006 | Neumann et al. |
| 2007/0088398 | A1 * | 4/2007 | Jacobson .................. 607/9 |
| 2007/0093786 | A1 | 4/2007 | Goldsmith et al. |
| 2007/0253021 | A1 | 11/2007 | Mehta et al. |

(Continued)

OTHER PUBLICATIONS

Reply to Written Opinion of international application No. PCT/US2011/034655, dated Nov. 17, 2011, 9 pp.

(Continued)

*Primary Examiner* — Kennedy Schaetzle
(74) *Attorney, Agent, or Firm* — Michael C. Soldner (57) ABSTRACT Various techniques for disabling a first implantable medical device (IMD) by modulation of therapeutic electrical stimulation delivered by a second medical device are described. One example method includes delivering therapeutic electrical stimulation from a more recently implanted second IMD at a higher average rate than the previously implanted first IMD so that only the more recently implanted IMD will administer therapy, and modulating stimulation by the more recently implanted IMD in order to send a disable command to the previously implanted IMD.

26 Claims, 6 Drawing Sheets (56) References Cited

U.S. PATENT DOCUMENTS

2007/0254593 A1 11/2007 Jollota et al.
2008/0109050 A1 5/2008 John
2009/0062879 A1 3/2009 Li et al.
2009/0171410 A1 7/2009 Benarie
2009/0227855 A1 9/2009 Hill et al.
2010/0114250 A1 5/2010 Zdeblick
2010/0249883 A1 9/2010 Zdeblick

OTHER PUBLICATIONS

International Search Report and Written Opinion of international application No. PCT/US2011/034655, dated Jul. 7, 2011, 10 pp.
International Preliminary Report on Patentability from corresponding PCT Application No. PCT/US2011/034655 dated Mar. 12, 2013 (9 pages).

\* cited by examiner

DISABLING AN IMPLANTED MEDICAL DEVICE WITH ANOTHER MEDICAL DEVICE

This application claims the benefit of U.S. Provisional Application Ser. No. 61/437,460, filed Jan. 28, 2011, the entire content of which is incorporated herein by reference.

TECHNICAL FIELD

The disclosure relates to implantable medical devices, and more particularly, to methods for disabling implantable medical devices.

BACKGROUND

A wide variety of medical devices for delivering therapy or monitoring a physiological condition have been used clinically or proposed for clinical use in patients. Examples include medical devices that deliver therapy to and/or monitor conditions associated with the heart, muscle, nerve, brain, stomach or other organs or tissue. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient.

Implantable cardiac pacemakers or cardioverter-defibrillators, for example, provide therapeutic electrical signals to the heart, e.g., via electrodes carried by one or more implantable medical leads. The therapeutic electrical signals may include pulses for pacing, or shocks for cardioversion or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an implantable medical device may deliver pacing stimulation to the heart of the patient upon detecting tachycardia or bradycardia, and deliver cardioversion or defibrillation shocks to the heart upon detecting fibrillation.

Leadless implantable medical devices may also be used to deliver therapy to a patient, and/or sense physiological parameters of a patient. In some examples, a leadless implantable medical device may include one or more electrodes on its outer housing to deliver therapeutic electrical signals to a patient, and/or sense intrinsic electrical signals of a patient. For example, a leadless cardiac device, e.g., pacemaker, may be used to sense intrinsic depolarizations or other physiological parameters of the heart, and/or deliver therapeutic electrical signals to the heart. Leadless cardiac devices may be positioned within or outside of the heart and, in some examples, may be anchored to a wall of the heart via a fixation mechanism.

SUMMARY

In general, this disclosure describes techniques for disabling an implanted medical device with another medical device. In some examples, a first implanted medical device is disabled by a second implanted medical device. The second medical device may modulate a therapeutic electrical stimulation in a way that is detectable by the first medical device as a command. In response to receipt of the command, the first medical device may be disabled. For example, a more recently implanted pacemaker may modulate pacing pulses in a way that is detectable as a command by a previously implanted and/or malfunctioning pacemaker. In response to the modulated pacing, the previously implanted and/or malfunctioning pacemaker may be disabled. The pacemakers may be leadless pacemakers.

If a power source of an implantable medical device (IMD) becomes depleted, or if a communication module of the IMD becomes unresponsive to external communication, a replacement IMD may be implanted. Therapeutic electrical stimulation delivered by the replacement IMD may be modulated to disable the previously implanted IMD. The ability to disable a previously implanted IMD using a modulated electrical stimulation in a newly implanted IMD may be particularly advantageous in situations in which other means of communication with the previously implanted IMD, e.g., radio-frequency or inductive communication via an external computing device, are no longer available or reliable. The ability to disable a previously implanted IMD may also be particularly advantageous in situations in which the previously implanted IMD is relatively difficult to explant, such as a leadless pacemaker implanted on or within the heart.

In one example, the disclosure is directed to a system comprising a first implantable medical device coupled to a first plurality of electrodes, wherein the first implantable medical device is configured to deliver therapeutic electrical stimulation to a patient via the first plurality of electrodes, and a second medical device coupled to a second plurality of electrodes. The second medical device is configured to deliver therapeutic electrical stimulation to the patient via the second plurality of electrodes to inhibit the delivery of therapeutic electrical stimulation by the first implantable medical device, and modulate the therapeutic electrical stimulation delivered by the second implantable medical device according to a predetermined pattern to provide a disable command to the first implantable medical device. The first implantable medical device is disabled in response to receipt of the disable command.

In another example, the disclosure is directed to an implantable medical device comprising a housing, a therapy delivery module within the housing, wherein the therapy delivery module is coupled to a plurality of electrodes and configured to deliver therapeutic electrical stimulation to a patient via the electrodes, and a processor within the housing. The processor is configured to control the therapy delivery module to deliver the therapeutic electrical stimulation to inhibit delivery of therapeutic electrical stimulation by another implantable medical device, and modulate the therapeutic electrical stimulation according to a predetermined pattern to provide a disable command to the other implantable medical device. The other implantable medical device is disabled in response to receipt of the disable command.

In another example, the disclosure is directed to a method comprising delivering therapeutic electrical stimulation from a medical device to a patient via a plurality of electrodes to inhibit delivery of therapeutic electrical stimulation to the patient by another implantable medical device, and modulating the therapeutic electrical stimulation delivered by the medical device according to a predetermined pattern to provide a disable command to the other implantable medical device. The other implantable medical device is disabled in response to receipt of the disable command.

In another example, a method for disabling a first medical device previously implanted within a patient with a second implanted medical device more recently implanted in the patient comprises controlling a therapy delivery module of the more recently implanted medical device to deliver a signal to the patient via at least one electrode that is coupled to the more recently implanted medical device and implanted within the patient, and modulating the signal by the more recently implanted medical device to provide a disable command to the previously implanted medical device. The method further comprises detecting the signal by the previously implanted medical device via at least one electrode that is coupled to the previously implanted medical device and implanted within the patient and a sensing module of the previously implanted medical device that is configured to detect intrinsic electrical activity of the patient via the electrode, and identifying, by the previously implanted medical device, the disable command within the detected signal. The previously implanted medical device is disabled in response receipt of the disable command.

The details of one or more examples are set forth in the accompanying drawings and the description below. Other features, objects, and advantages will be apparent from the description and drawings, and from the claims.

DETAILED DESCRIPTION

As power sources in IMDs with leads become depleted, typically they are explanted. For example, a pacemaker with leads implanted in the heart of a patient has a separate enclosure that is attached to the proximal end of the leads. This enclosure is often located near the skin of the patient, and can be accessed with minimally invasive procedures. If the power source of an IMD has reached its end of life, or if the IMD is otherwise malfunctioning, the IMD can be replaced with a new IMD by detaching the proximal end of the leads and removing the old IMD.

Once an IMD has reached its end of life or has malfunctioned, it may be desirable to disable the IMD, e.g., before it is explanted. This may be desired in order to ensure that the IMD does not begin to act erratically due to the unpredictable effects of a depleted power source on a processor in the IMD or for other reasons. For example, without the correct voltage or current, a processor may be unable to correctly detect when a patient requires delivery of therapeutic electrical stimulation.

A pacemaker, for example, may fail to detect an abnormal rhythm, and subsequently fail to provide the appropriate stimulation signal to return the heart to a normal rhythm. Likewise, the pacemaker may falsely detecting an abnormal rhythm, e.g., incorrectly interpret a normal rhythm to be an arrhythmia, and administer unnecessary pulses or shocks to the patient's heart. Finally, a pacemaker may correctly identify an abnormal rhythm, but then incorrectly calculate the appropriate stimulation in response to the abnormal rhythm.

To avoid these problems, IMDs may include software to disable the device after a communication module, e.g., for radio-frequency or inductive communication with an external computing device, receives an external "disable" command. If the communication module fails, though, the external disable command would not be received and relayed to the software or firmware, and the IMD would fail to shut down. The IMD would then continue to operate until the power source was depleted.

Leadless pacemakers are generally designed to be permanently implanted in a patient's heart. They generally are not intended to be removed, and would require a relatively invasive surgery to do so. Advances in the miniaturization of power sources and operational circuitry are such that once a leadless pacemaker reaches end of life, a new leadless pacemaker may be implanted to replace it, without explanting the original pacemaker. If a communication module in a leadless pacemaker fails, and it is unable to receive an external disable command, the pacemaker would continue to run until the power source was depleted. As previously noted, erratic behavior can ensue if a power source becomes too depleted. An invasive surgery would have to be performed to remove the leadless pacemaker.

In general, this disclosure describes techniques for disabling a first implanted medical device with a second implanted medical device. In some examples, the techniques include modulating the delivery of therapeutic electrical stimulation by a second IMD in such a way as to provide a disable command to a first IMD. In some examples, one or both of the first and second implanted medical devices are leadless pacemakers. If a communication module malfunctions, or the power source in a leadless pacemaker simply becomes depleted at its end of life, a new leadless pacemaker may be implanted in the same patient. Once activated, the newly implanted pacemaker may be configured to modulate the delivery of pacing in such a way that the old pacemaker senses the modulation. The old pacemaker may be configured to interpret this therapy modulation as a disable command.

As described in more detail below, a variety of aspects of the therapeutic electrical stimulation may be modulated to provide the disable command. As examples, the amplitude or frequency of the electrical stimulation may be modulated. If the stimulation is delivered in the form of pulses, the width of the pulses may additionally or alternatively be modulated. Modulation may include varying the signal parameter between two values, e.g., amplitude, frequency, or pulse width values, in a predetermined pattern recognizable by the first IMD as a disable command.

In some examples, other aspects of the morphology of stimulation pulses may be modulated, such as the number, width, interval between, or order of polarities of phases for biphasic or multiphasic pulses. In one example, the intervals between pulses delivered by the second IMD, e.g., pacing pulses, may be dithered, e.g., between two lengths, in a predetermined pattern recognizable by the first IMD as a disable command. In some examples, the second IMD may deliver one or more additional pulses, e.g., pacing pulses, during a refractory period of the tissue to which therapeutic electrical stimulation is delivered, e.g., a refractory period of the heart. Pulses delivered during the refractory period of the heart, for example, may not capture the heart or otherwise provide therapy. The presence or absence, number, amplitude, or width of such additional pulses, or intervals between such pulses, or intervals between such pulses and pacing pulses, may be modulated by the second IMD to provide a disable command to the first IMD.

Figure 1:
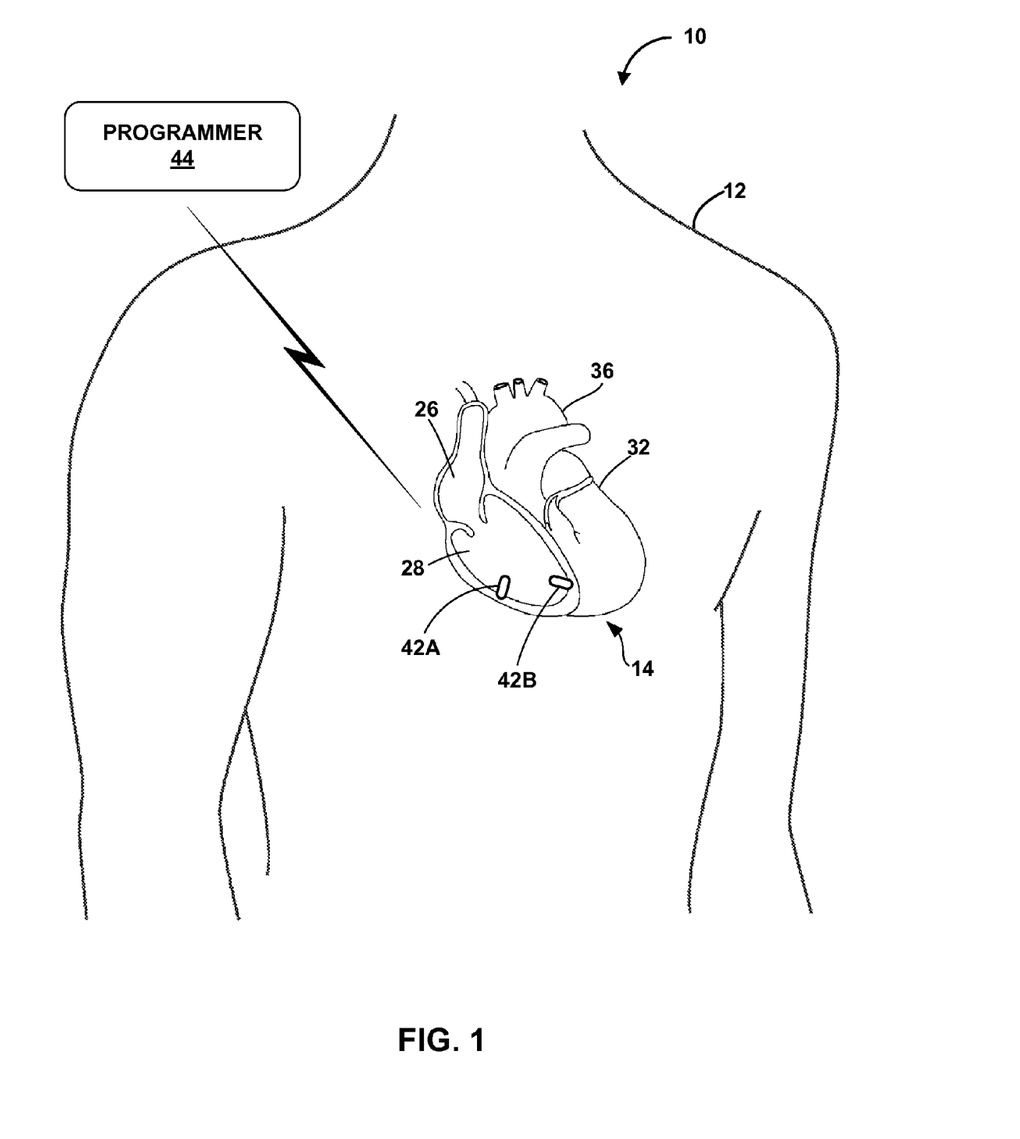
FIG. 1 is a conceptual diagram illustrating an example system comprising first and second leadless implantable medical devices (IMDs) implanted within the heart.

FIG. 1 is a conceptual diagram illustrating an example system 10 that may be used to monitor one or more physiological parameters of patient 12 and/or to provide therapy to heart 14 of patient 12. System 10 includes a first implantable medical device (IMD) 42A and a second IMD 42B (collectively "IMDs 42") implanted within heart 14. IMDs 42 may be implantable leadless pacemakers that provide electrical signals to heart 14 via one or more electrodes (not shown in FIG. 1) on their outer housing. IMDs 42 may sense electrical signals attendant to the depolarization and repolarization of heart 14 via electrodes on their outer housing, and provide pacing pulses to heart 14 based on the electrical signals sensed within heart 14. Patient 12 is ordinarily, but not necessarily, a human patient.

In the example of FIG. 1, IMDs 42 are positioned wholly within heart 14 proximate to an inner wall of right ventricle 28 to provide right ventricular (RV) pacing. Although IMDs 42 are shown within heart 14 and proximate to an inner wall of right ventricle 28 in the example of FIG. 1, IMDs 42 may be positioned together or separately at any other location outside or within heart 14. For example, IMDs 42 may be positioned outside or within right atrium 26, left atrium 36, and/or left ventricle 32, e.g., to provide right atrial, left atrial, and left ventricular pacing, respectively. Depending in the location of implant, IMDs 42 may include other stimulation functionalities. For example, IMDs 42 may provide atrioventricular nodal stimulation, fat pad stimulation, vagal stimulation, or other types of neurostimulation. In various examples, system 10 may include any number of leadless IMDs 42, e.g., to provide stimulation and/or sensing at a variety of locations.

FIG. 1 further depicts a programmer 44 in communication with IMDs 42. In some examples, programmer 44 comprises a handheld computing device, computer workstation, or networked computing device. Programmer 44 includes a user interface that presents information to and receives input from a user. It should be noted that the user may also interact with programmer 44 remotely via a networked computing device.

A user, such as a physician, technician, surgeon, electrophysiologist, other clinician, or patient, interacts with programmer 44 to communicate with IMDs 42. For example, the user may interact with programmer 44 to retrieve physiological or diagnostic information from IMDs 42. A user may also interact with programmer 44 to program IMDs 42, e.g., select values for operational parameters of the IMDs 42. For example, the user may use programmer 44 to retrieve information from IMDs 42 regarding the rhythm of heart 14, trends therein over time, or arrhythmic episodes.

In some examples, the user may use programmer 44 to retrieve information from IMDs 42 regarding other sensed physiological parameters of patient 12 or information derived from sensed physiological parameters, such intracardiac or intravascular pressure, activity, posture, respiration, tissue perfusion, heart sounds, or a cardiac electrogram (EGM), intracardiac impedance, or thoracic impedance. In some examples, the user may use programmer 44 to retrieve information from IMDs 42 regarding the performance or integrity of IMDs 42 or other components of system 10, or a power source of IMDs 42. As another example, the user may interact with programmer 44 to program, e.g., select parameters for therapies provided by IMDs 42, such as pacing and, optionally, neurostimulation.

IMDs 42 and programmer 44 may communicate via wireless communication using any techniques known in the art.

Examples of communication techniques may include, for example, low frequency or radiofrequency (RF) telemetry, but other techniques are also contemplated.

In some examples, IMD 42A may be a previously implanted pacemaker that has malfunctioned, or reached its end of life. As a result, IMD 42B may be implanted to continue delivering pacing therapy to the patient. IMD 42B may be configured to pace at a higher rate than IMD 42A, preventing IMD 42A from delivering therapy. IMD 42A may be configured to recognize a disable command from IMD 42B in the form of modulated therapy delivered by IMD 42B. IMD 42B may be configured to modulate the therapy it delivers in a predetermined pattern to provide the disable command. Once the modulated therapy signal is received, IMD 42A would be disabled. Using the techniques of this disclosure, modulation of therapy delivery may be used to disable a leadless pacemaker.

Figure 2:
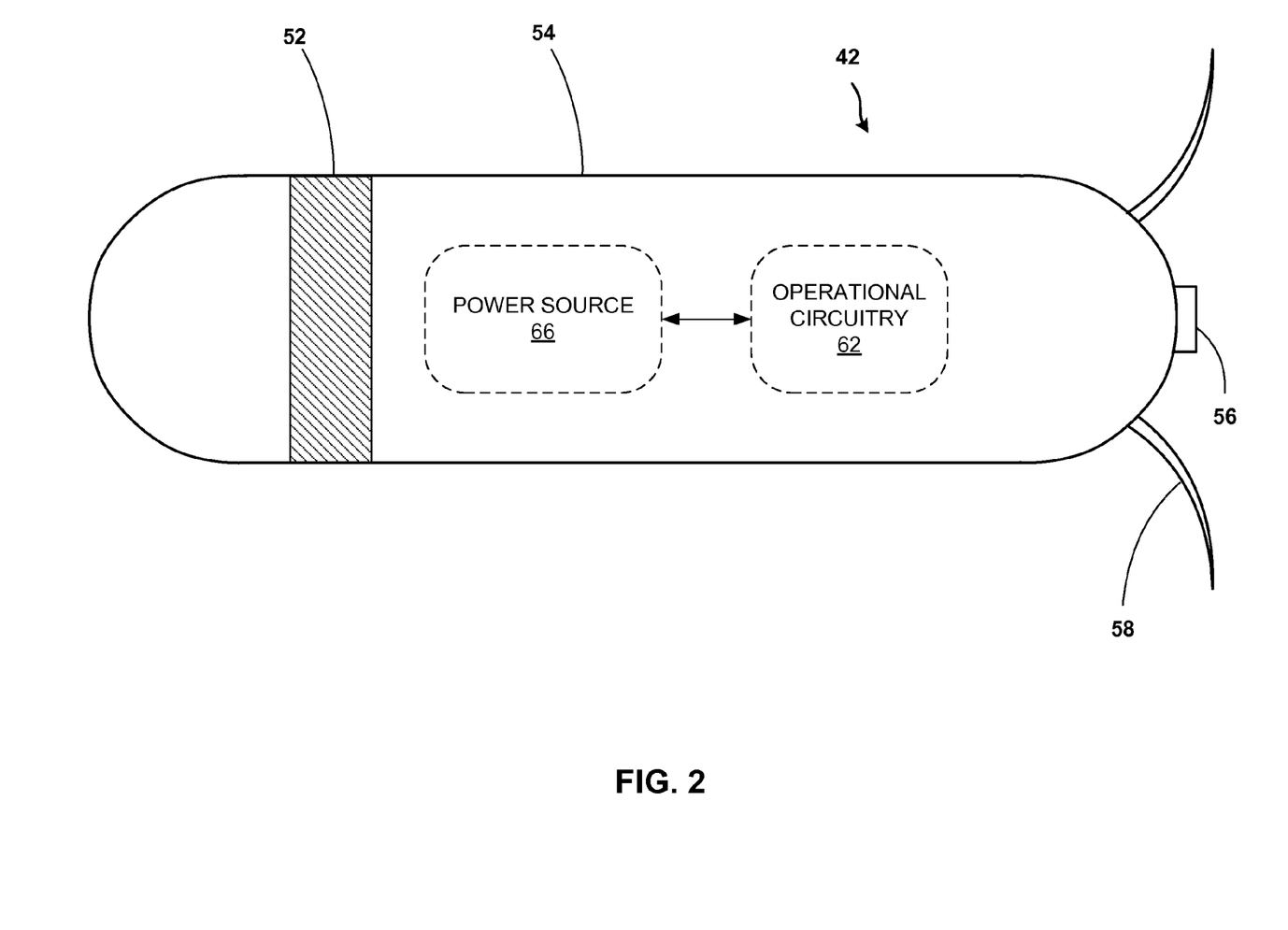
FIG. 2 is a conceptual diagram further illustrating an example leadless IMD.

FIG. 2 is a conceptual diagram illustrating a leadless IMD 42 in further detail. IMD 42 of FIG. 2 may correspond to either or both of IMDs 42 in FIG. 1. In the example of FIG. 2, leadless IMD 42 includes fixation mechanism 58. Fixation mechanism 58 may anchor leadless IMD 42 to a wall of heart 14. For example, fixation mechanism 58 may take the form of a plurality of tines. Alternatively, other structures of fixation mechanism 58, e.g., a helical structure that may be screwed into a wall of heart 12, may be utilized. In some examples, fixation mechanism 58 is conductive and may be used as an electrode, e.g., to deliver therapeutic electrical signals to heart 14 and/or sense intrinsic depolarizations of heart 14.

Leadless IMD 42 may also include electrodes 52 and 56 on its outer housing 54. Electrodes 52 and 56 may be used to deliver therapeutic electrical signals to heart 14 and/or sense intrinsic depolarizations of heart 14. Electrodes 52 and 56 may be formed integrally with an outer surface of hermetically-sealed housing 54 of IMD 42 or otherwise coupled to housing 54. In this manner, electrodes 52 and 56 may be referred to as housing electrodes. In some examples, housing electrodes 52 and 56 are defined by uninsulated portions of an outward facing portion of housing 54 of IMD 42. Other division between insulated and uninsulated portions of housing 54 may be employed to define a different number or configuration of housing electrodes. For example, in an alternative configuration, IMD 42 may include a single housing electrode that comprises substantially all of housing 54, and may be used in combination with an electrode formed by fixation mechanism 58 for sensing and/or delivery of therapy. Leadless IMD 42 may include power source 66 electrically coupled to operational circuitry element 62.

Figure 3:
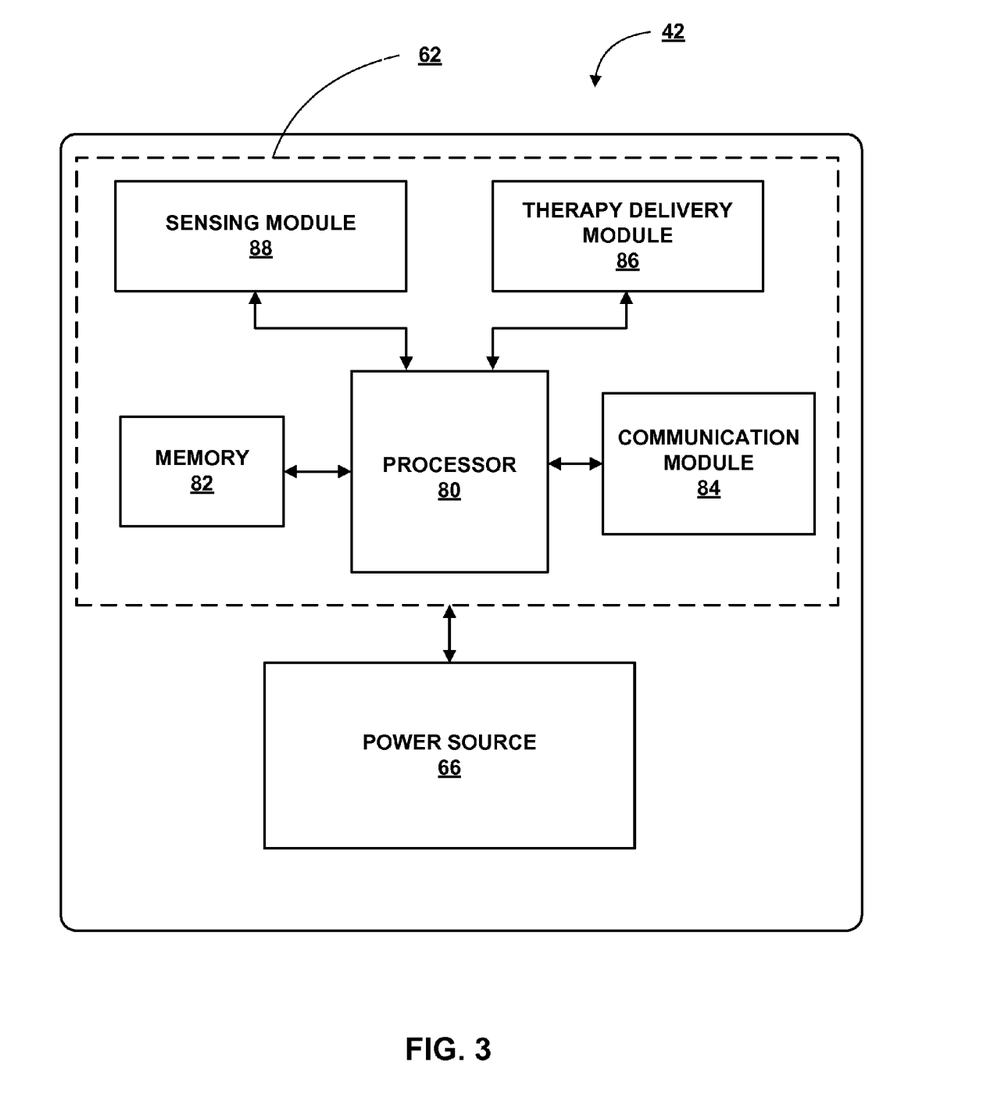
FIG. 3 is a functional block diagram illustrating an example configuration of the IMD of FIG. 2.

FIG. 3 is a functional block diagram illustrating one example configuration of IMD 42 of FIG. 2 in further detail. More specifically, FIG. 3 illustrates operational circuitry element 62 of FIG. 2 in further detail. In the example illustrated by FIG. 3, operational circuitry element 62 of IMD 42 includes a processor 80, memory 82, therapy delivery module 86, sensing module 88, and communication module 84.

Memory 82 may include computer-readable instructions that, when executed by processor 80, cause IMD 42 and processor 80 to perform various functions attributed to IMD 42 and processor 80 herein. Memory 82 may be a computer-readable storage medium, including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 in this disclosure may be embodied as software, firmware, hardware or any combination thereof. Processor 80 controls therapy delivery module 86 to deliver stimulation therapy to heart 14 according to operational parameters or programs, which may be stored in memory 82. For example, processor 80 may control therapy delivery module 86 to deliver electrical pulses with the amplitudes, pulse widths, frequency, or electrode polarities specified by the operational parameters, and at times or in response to sensed events or conditions as specified by the operational parameters.

Therapy delivery module 86, as well as sensing module 88, are electrically coupled to the electrodes of IMD 42, e.g., electrodes 56 and 58 (FIG. 2) via conductors disposed within housing 54 (FIG. 2) of IMD 42. In examples in which fixation mechanism 58 functions as an electrode, therapy delivery module 86 and sensing module 88 may similarly be coupled to fixation mechanism 58 (FIG. 2) via a conductor disposed within housing 54 (FIG. 2) of IMD 42.

In the example illustrated in FIG. 3, therapy delivery module 86 is configured to generate and deliver electrical stimulation therapy to heart 14. For example, therapy delivery module 86 may deliver pacing, and/or neurostimulation therapy via at least a subset of the available electrodes. In some examples, therapy delivery module 86 delivers one or more of these types of stimulation in the form of electrical pulses. In other examples, therapy delivery module 86 may deliver one or more of these types of stimulation in the form of other signals, such as sine waves, square waves, or other substantially continuous time signals.

Sensing module 88 monitors signals from at least a subset of the available electrodes in order to monitor electrical activity of heart 14. In some examples, sensing module 88 includes multiple detection channels, each of which may comprise an amplifier. Each sensing channel may detect electrical activity in respective chambers of heart 14, and may be configured to detect either R-waves or P-waves. In some examples, electrical sensing module 88 or processor 80 may include an analog-to-digital converter for digitizing the signal received from a sensing channel for electrogram (EGM) signal processing by processor 80.

During pacing, an escape interval counter maintained by processor 80 may be reset upon sensing of R-waves or P-waves by sensing module 88. Processor 80 may control therapy delivery module 86 to deliver a pacing pulse heart 14 upon expiration of an escape interval. Processor 80 may reset the escape interval counter upon the generation of pacing pulses by therapy delivery module 86, or detection of an intrinsic depolarization in a chamber, and thereby control the basic timing of cardiac pacing functions. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect heart rate, such as an atrial rate or ventricular rate.

Communication module 84 includes any suitable hardware, firmware, software or any combination thereof for communicating with another device, such as programmer 44 (FIGS. 1A and 1B). Under the control of processor 80, communication module 84 may receive downlink telemetry from and send uplink telemetry to programmer 44 with the aid of an antenna, which may be internal and/or external. Processor 80 may provide the data to be uplinked to programmer 44 and receive downlinked data from programmer 44 via an address/data bus. In some examples, communication module 84 may provide received data to processor 80 via a multiplexer.

In some examples, a user may attempt to disable IMD 42A by sending an external disable command via programmer 44. The external disable command from programmer 44 may be sent via an RF, inductive or another wireless communication medium, and may be receivable by IMD 42A via communication module 84, e.g., via an antenna of the communication module. In some examples, IMD 42A or communication module 84 may not be able to receive or respond to such an external disable command, e.g., when IMD 42A is nearing the end of its battery life, or otherwise not functioning optimally.

In some examples, IMD 42A may be configured to receive a disable command that is provided by IMD 42B. IMD 42B may provide the command by modulating an aspect of therapeutic electrical stimulation delivered by IMD 42B in a predetermined pattern. For example, processor 80 may be configured to control therapy delivery module 86 to modulate the interval between stimulation pulses, e.g., pacing pulses, to provide the disable command. In the case of pacing pulses, processor 80 may be configured to modify an escape interval between two values in a predetermined pattern to provide the disable command to IMD 42A. In some examples, processor 80 control therapy delivery module 86 to deliver a series of pulses with one interval length therebetween, e.g., at a first frequency, and then another series of pulses with another interval length therebetween, e.g., at a second frequency. These runs of pulses may serve as the modulation, and be recognizable as a disable command by IMD 42A.

The modulation of the therapeutic stimulation, e.g., the modification of the escape interval between pacing pulses, may be therapeutically insignificant. In other words, the patient may still receive adequate therapy during the modulation of the therapeutic stimulation, i.e., IMD 42B may simultaneously provide therapy to patient 12 and send a disable command to IMD 42A.

Sensing module 88 of IMD 42A may be configured to detect the delivery of therapeutic electrical stimulation by IMD 42B. For example, one or more sensing channels of sensing module 88 may be configured to detect the stimulation, and provide a signal indicating the occurrence of the stimulation to processor 80 of IMD 42A. An amplifier of a narrow-band channel of sensing module 88 of IMD 42A, for example, may be configured to provide a signal to processor 80 of IMD 42A upon detection of a pacing pulse. The amplifier may be configured with a threshold and one or more filters to detect pacing pulses, and reject other signals. Processor 80 of IMD 42A may determine intervals between, or frequency of, pacing pulses based on the indications from sensing module 88 of IMD 42A

In some examples, sensing module 88 of IMD 42A may digitize a sensed signal, and processor 80 of IMD 42A may perform digital signal analysis to identify the electrical stimulation, e.g., the occurrence of pacing pulses, delivered by IMD 42B. The processor may also perform digital signal analysis to identify characteristics of the electrical stimulation. The characteristics may include, for example, amplitude, width, or morphology of the signals, e.g., pulses, delivered by IMD 42B.

In some cases, when IMD 42B is directed, e.g., via programmer 44, to send a disable command to IMD 42A, IMD 42A may be delivering therapeutic electrical stimulation. In such cases, IMD 42B may need to assume control of the delivery of therapeutic electrical stimulation from IMD 42A. In examples in which IMDs 42 are pacemakers delivering pacing to heart 14, IMD 42A may be delivering pacing at a first rate, or heart 14 may be intrinsically depolarizing and beating at a first rate. In such examples, processor 80 of IMD 42B may determine the rate, and pace at a second, higher rate in order to ensure that IMD 42B, rather than IMD 42A is delivering pacing pulses. The delivery of pacing pulses by IMD 42B at the higher rate may ensure that the escape interval of IMD 42A does not expire, thereby inhibiting delivery of pacing by IMD 42A. Pacing by IMD 42B and inhibition of IMD 42A may facilitate delivery of the disable command by IMD 42B and receipt of the disable command by IMD 42A.

Figure 4A:
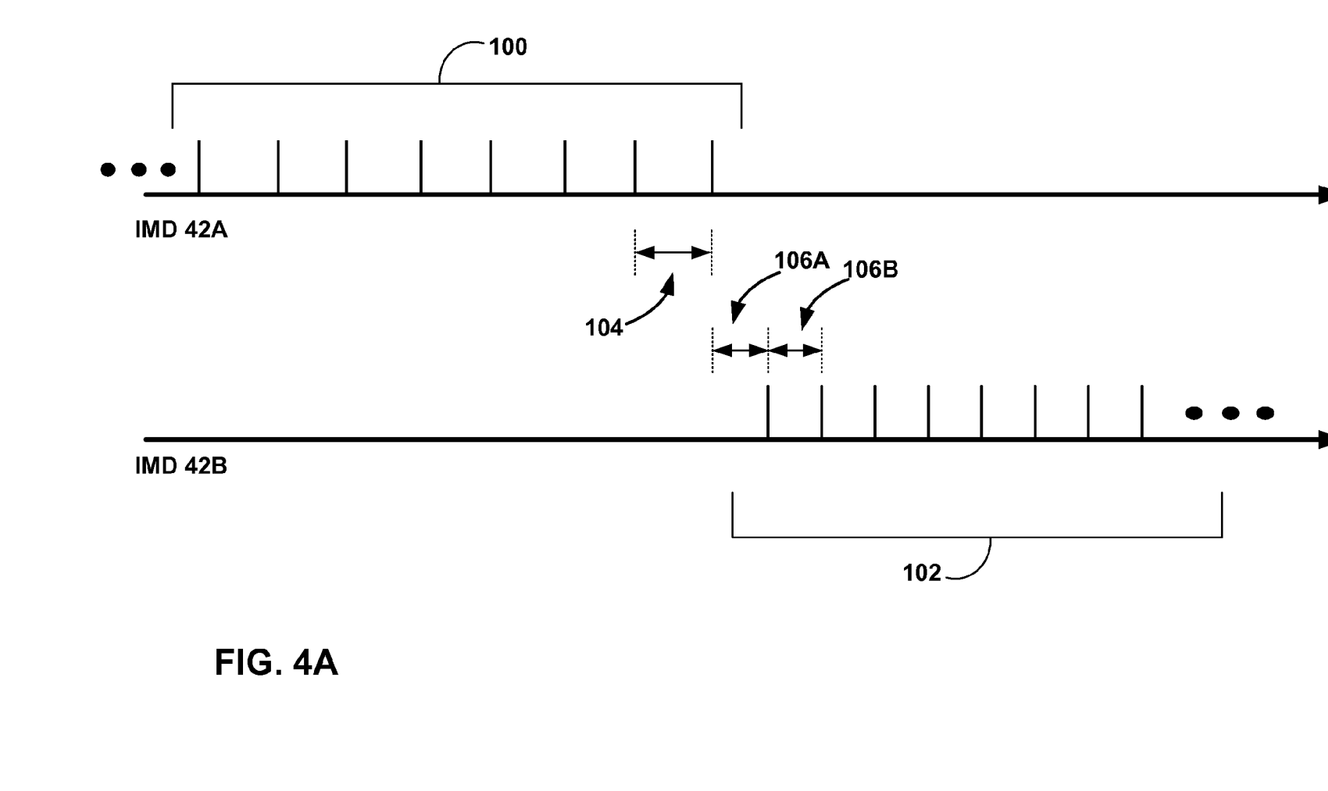
FIG. 4A is a timing diagram illustrating a second IMD assuming control of delivery of therapeutic electrical stimulation from a first IMD.

FIG. 4A is a timing diagram illustrating second IMD 42B assuming control of delivery of therapeutic electrical stimulation from first IMD 42A. As illustrated in FIG. 4A, IMD 42A delivers electrical stimulation pulses 100, e.g., pacing pulses, but then stops delivering the pulses when IMD 42B begins delivering electrical stimulation pulses 102, e.g., pacing pulses. The stimulation pulses 100 and 102 may both be therapeutic, and both delivered to achieve the same therapeutic effect. For example, pulses 100 and 102 may both be pacing pulses intended to pace the same chamber of heart 14. Pulses 100 delivered by IMD 42A have a first rate or frequency, and therefore have a first interval 104 therebetween. Although the example of FIG. 4A illustrates the situation in which IMD 42A is delivering therapeutic electrical stimulation pulses 100, e.g., pacing pulses, in other examples intrinsic depolarizations of heart 14 may additionally or alternatively precede delivery of pulses by IMD 42B.

In order to capture heart 14 and assume control of the delivery of therapy from IMD 42A, IMD 42B delivers pulses 102 at a higher rate than the rate of pulses 100 or intrinsic depolarizations, e.g., delivers overdrive pacing. Thus, the interval 106A between the last pulse delivered by IMD 42A (or intrinsic depolarization of heart 14) and the first pulse 102 delivered by IMD 42B is less than the interval 104 between pulses 100. Further, the interval 106B between pulses 102 delivered by IMD 42B is less than the interval 104 between pulses 100. In this manner, IMD 42B may ensure that it delivers stimulation pulses, and inhibit the delivery of stimulation pulses by IMD 42A and intrinsic depolarizations of heart 14.

Figure 4B:
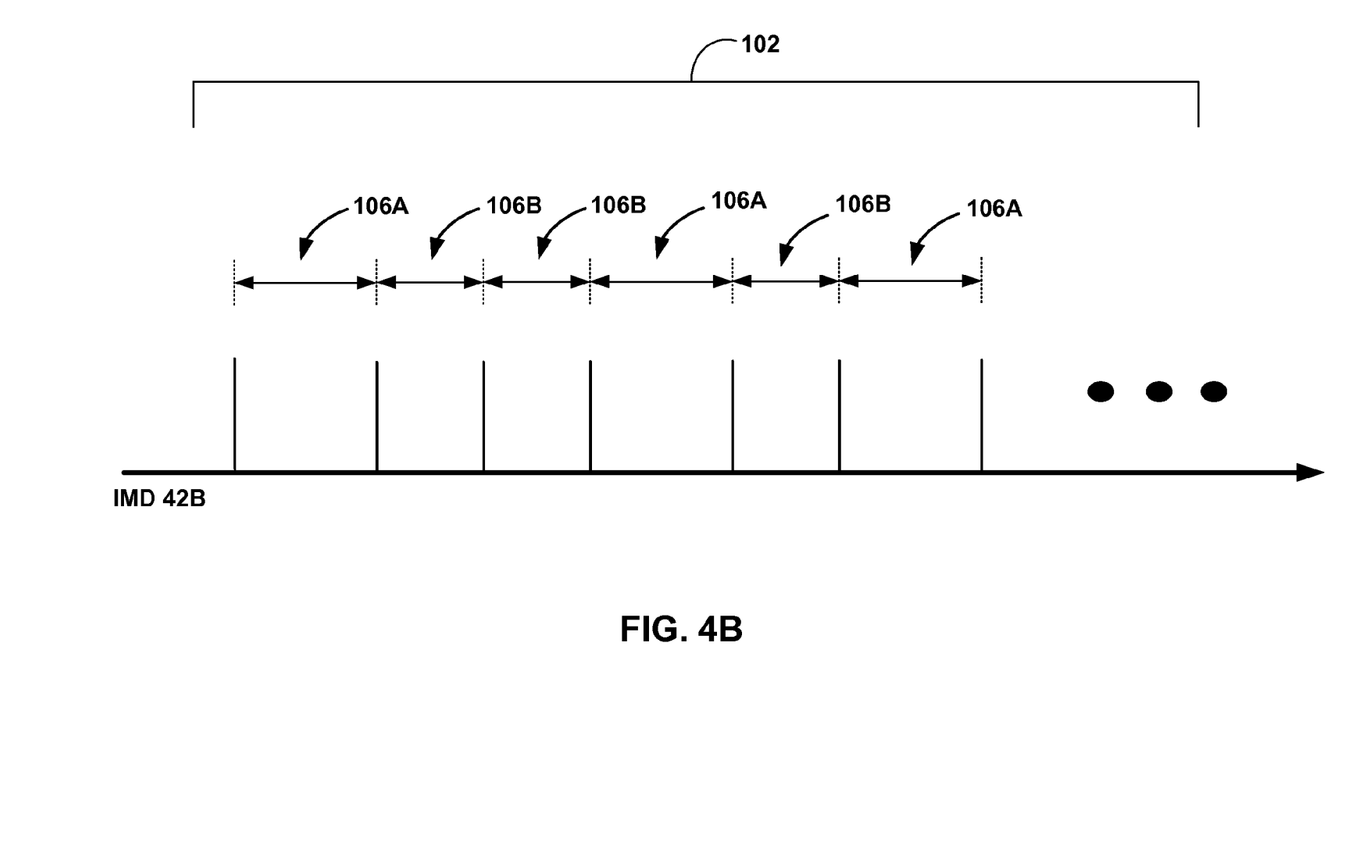
FIG. 4B is a timing diagram illustrating modulation of therapeutic electrical stimulation by a second IMD to provide a disable command to a first IMD

FIG. 4B is a timing diagram illustrating modulation of therapeutic electrical stimulation by second IMD 42B to provide a disable command to a first IMD 42A. In particular, FIG. 4B further illustrates pulses 102 delivered by IMD 42B. As illustrated by FIG. 4B, IMD 42B modulates the length of the interval between pulses 102 between a first length 106A and a second length 106B. Processor 80 of IMD 42B may control the timing of delivery of pulses 102 by therapy delivery module 88 of IMD 42B, e.g., may dither the timing of the pulses, to achieve the different interval lengths 106A and 106B. In some examples, processor 80 of IMD 42B may vary an escape interval between two values to achieve the different interval lengths 106A and 106B.

The pattern of interval lengths 106A and 106B may be detectable by IMD 42A and recognizable by IMD 42A as a disable command. IMD 42B may store the pattern, e.g., instructions to achieve the pattern, within its memory 82, such that it is available to processor 80. In some examples, processor 80 of IMD 42B may receive the pattern or instructions for producing the patter from programmer 44 via communication module 84, e.g., via wireless telemetry.

If a user tries to send an external disable command to communication module 84 (e.g., RF telemetry module of IMD 42A via programmer 44, and IMD 42A does not respond, the user may direct IMD 42B to provide a disable command to IMD 42A according to the techniques of this disclosure. The ability of IMD 42A to detect and respond to a therapy delivery modulation signal may allow an additional fail-safe for medical devices near end of life. The ability to detect and respond to therapy delivery modulation may also provide an additional fail-safe for a medical device that is not at end of life, but in which normal telemetry communications have failed.

Figure 5:
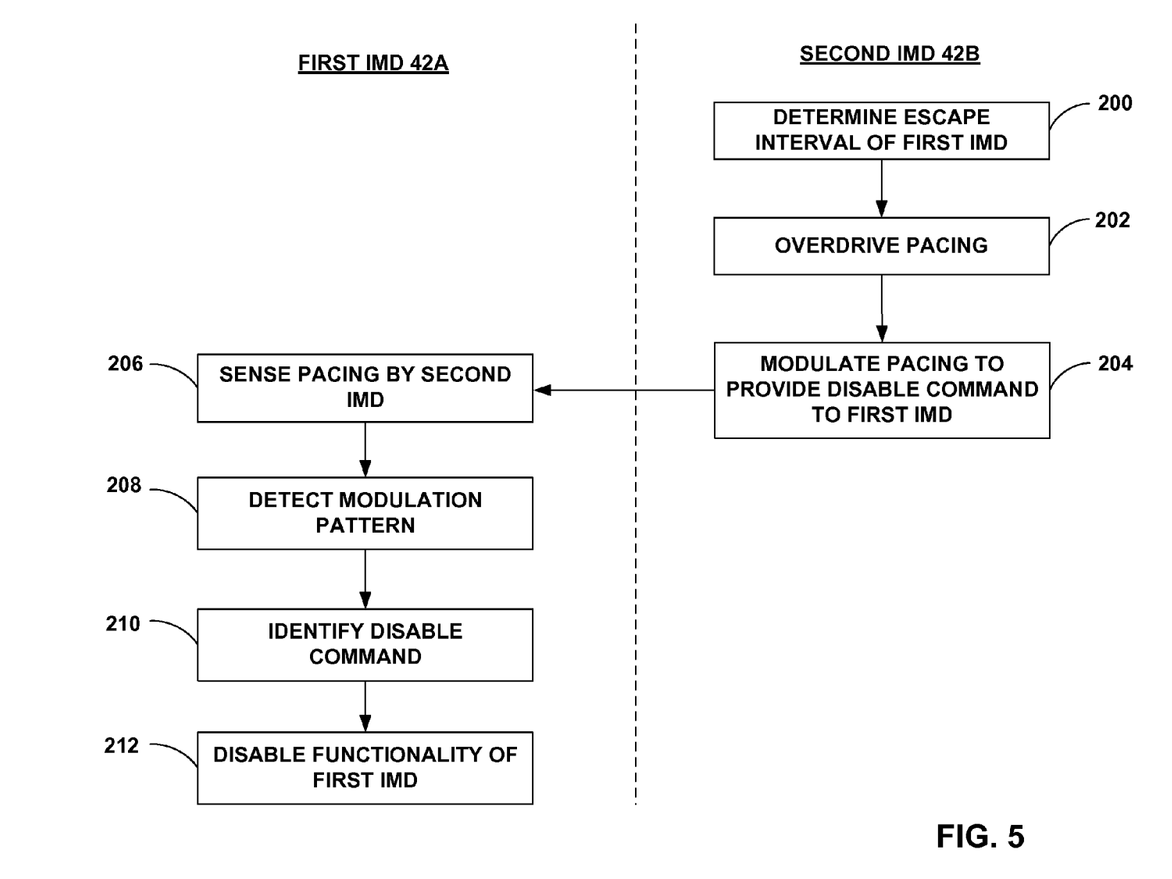
FIG. 5 is a flow diagram illustrating an example method for a second IMD to provide a disable command to a first IMD by modulating therapeutic electrical stimulation.

FIG. 5 is a flow diagram illustrating an example method for a second IMD to provide a disable command to a first IMD by modulating therapeutic electrical stimulation. In the example of FIG. 5, IMDs 42A and 42B are pacemakers that deliver pacing pulses to provide therapeutic electrical stimulation. The techniques described herein may be applicable to other types of therapeutic electrical stimulation, however.

According to the example method of FIG. 5, IMD 42B determines an escape interval of IMD 42A (200). IMD 42B may determine the escape interval by monitoring delivery of pacing pulses by IMD 42A, or by receiving an indication of the escape interval from programmer 44, as examples. In some examples, IMD 42B may determine an intrinsic rate of heart 14, e.g., an average rate, by monitoring a cardiac electrogram signal.

In either case, IMD 42B begins overdrive pacing (202) by delivering pacing pulses at a rate that is greater than the rate of pacing by IMD 42A or rate of intrinsic depolarizations of heart 14. In some examples, IMD 42B provides overdrive pacing by pacing with an escape interval that is shorter than the escape interval used by IMD 42A. While overdrive pacing, IMD 42B modulates the pacing to provide a disable command to IMD 42A (204). For example, IMD 42B may dither the timing of pacing, e.g., by switching between two or more escape interval values, in a predetermined pattern. The predetermined pattern is a disable command recognizable by IMD 42A.

Delivery of pacing by IMD 42A is inhibited by the overdrive pacing by IMD 42B. IMD 42A senses the pacing by IMD 42B (206). For example, a sensing module 88 of IMD 42A may be configured to sense pacing pulses delivered by IMD 42B, and provide indications of the occurrence of the pacing pulses to the processor 80 of IMD 42A. Processor 80 of IMD 42A may detect an aspect of the pacing pulses delivered by IMD 42B, such as intervals between the pacing pulses.

IMD 42A, e.g., processor 80 of the IMD, detects a modulation pattern in the pacing pulses delivered by IMD 42B (208). For example, IMD 42A may detect a pattern of relatively longer and shorter intervals between the pacing pulses. Based on the pattern, IMD 42A, e.g., processor 80 of the IMD, identifies a disable command from IMD 42B (210). In response to the disable command, IMD 42A is disabled (212). Disabling of IMD 42A may include, for example, powering down the IMD, or disabling some functionality of IMD, such as therapy delivery and/or physiologic sensing.

In some examples, after delivery of the disable command, IMD 42B may suspend overdrive pacing. IMD 42B may begin to pace at a more physiologically optimal rate, such as according to the escape interval previously utilized by IMD 42A, under the assumption that IMD 42A is no longer pacing in response to the disable command. In some examples, IMD 42B may suspend therapy, or utilize an escape interval longer than that used by IMD 42A, for a period of time to determine whether IMD 42A has in fact suspended pacing. If IMD 42A paces during such a period, IMD 42B may repeat the technique of FIG. 5 to again provide the disable command to IMD 42A and/or provide an indication to a user via programmer 44.

In some examples, the disable command may be configured or supplemented to provide "false proofing," e.g., to prevent the first IMD, e.g., IMD 42A, from incorrectly interpreting noise detected by the first IMD as a disable command. For example, the disable command may include a cyclical redundancy check (CRC), may be repeated, and/or the like to provide false proofing for the disable command.

Various examples have been described. However, one of ordinary skill in the art will appreciate that various modifications may be made to the described examples without departing from the scope of the claims.

For example, although dithering the timing of therapeutic electrical stimulation pulses, e.g., the length of intervals between pulses, is the primary example of modulation of therapeutic electrical stimulation, any form of signal modulation may be used in conjunction with the techniques described herein. For example, the amplitude, frequency, phase, or width (e.g., in the case of pulses) of the therapeutic electrical signal may be modulated. In some examples, phase-shift keying, frequency-shift keying, amplitude-shift keying, or quadrature amplitude modulation may be employed. In some examples, pulse-amplitude modulation, pulse-width modulation, or pulse-position modulation may be employed. These or any other form of signal modulation may be employed to communicate a disable command from one implanted medical device to another implanted medical device according to the techniques described herein.

Furthermore, in some examples, the second implanted device may not need to assume control of the delivery of therapy from the first implantable medical device when providing the disable command and/or the disable command may not provide therapeutic electrical stimulation. For example, a second implanted medical device may deliver a signal, e.g., pulses, during one or more refractory periods, e.g., of the heart, and may modulate the pulses or other signal to provide the disable command. The signal delivered during the refractory period, which is modulated to provide the disable command, may not be therapeutic electrical stimulation because it is delivered during the refractory period when the patient tissue, e.g., heart, is not responsive to therapeutic electrical stimulation. In the case of the heart, the refractory periods may be subsequent to intrinsic depolarizations of the heart or delivery of pacing pulses by the first implanted medical device. Accordingly, the second implanted medical device may not need to assume control of the heart or the pacing of heart from the first implanted medical device when delivering the disable command.

Additionally, this disclosure has primarily focused on examples in which a second implanted or implantable medical device disables a first implanted medical device. In some examples, the first or second implantable medical devices may be temporarily implanted. Additionally, in other examples an external medical device may disable an implanted medical device according to the techniques described herein. These and other examples are within the scope of the following claims.

The invention claimed is:
1. A system comprising:
   a first implantable medical device coupled to a first plurality of electrodes, wherein the first implantable medical device is configured to deliver therapeutic electrical stimulation to a patient via the first plurality of electrodes; and
   a second medical device coupled to a second plurality of electrodes, wherein the second medical device is configured to:
      deliver therapeutic electrical stimulation to the patient via the second plurality of electrodes to inhibit the delivery of therapeutic electrical stimulation by the first implantable medical device; and
      modulate the therapeutic electrical stimulation delivered by the second implantable medical device according to a predetermined pattern to provide a disable command to the first implantable medical device,
   wherein the first implantable medical device is disabled in response to receipt of the disable command.

2. The system of claim 1, wherein the second medical device comprises a second implantable medical device.

3. The system of claim 1, wherein the first and second medical devices comprise first and second cardiac pacemakers, and the therapeutic electrical stimulation comprises cardiac pacing.

4. The system of claim 1, wherein the therapeutic electrical stimulation comprises pulses, the first implantable medical device delivers the pulses at a first rate, and the second medical device delivers the pulses at a second rate that is greater than the first rate to inhibit the delivery of pulses by the first implantable medical device.

5. The system of claim 1, wherein the therapeutic electrical stimulation comprises pulses, and the second medical device modulates a length of intervals between consecutive ones of the pulses to provide the disable command.

6. The system of claim 1, wherein the second medical device modulates at least one of an amplitude, frequency, or width of the therapeutic electrical stimulation to provide the disable command.

7. The system of claim 1, wherein the first implantable medical device comprises a housing that comprises the first plurality of electrodes, and the second medical device comprises a housing that comprises the second plurality of electrodes.

8. An implantable medical device comprising:
   a housing;
   a therapy delivery module within the housing, wherein the therapy delivery module is coupled to a plurality of electrodes and configured to deliver therapeutic electrical stimulation to a patient via the electrodes; and
   a processor within the housing, the processor configured to:
      control the therapy delivery module to deliver the therapeutic electrical stimulation to inhibit delivery of therapeutic electrical stimulation by another implantable medical device; and
      modulate the therapeutic electrical stimulation according to a predetermined pattern to provide a disable command to the other implantable medical device,
   wherein the other implantable medical device is disabled in response to receipt of the disable command.

9. The implantable medical device of claim 8, wherein the implantable medical device and the other implantable medical device comprise cardiac pacemakers, and the therapeutic electrical stimulation comprises cardiac pacing.

10. The implantable medical device of claim 8,
   wherein the therapeutic electrical stimulation comprises pulses, and the other implantable medical device delivers the pulses at a first rate, and
   wherein the processor is configured to control the therapy delivery module to deliver the pulses at a second rate that is greater than the first rate to inhibit the delivery of pulses by the other implantable medical device.

11. The implantable medical device of claim 10, further comprising a communication module to receive an indication of the first rate from an external programmer.

12. The implantable medical device of claim 10, further comprising a sensing module configured to sense the pulses, via the electrodes, delivered by the other implantable medical device, wherein the processor is configured to determine the first rate based on the pulses sensed by the sensing module.

13. The implantable medical device of claim 8, wherein the therapeutic electrical stimulation comprises pulses, and the processor controls the therapy delivery module to modulate a length of intervals between consecutive ones of the pulses to provide the disable command.

14. The implantable medical device of claim 13, wherein the therapeutic electrical stimulation comprises cardiac pacing, and the processor modulates an escape interval between a plurality of values to provide the disable command.

15. The implantable medical device of claim 8, wherein the processor controls the therapy delivery module to modulate at least one of an amplitude, frequency, or width of the therapeutic electrical stimulation to provide the disable command.

16. The implantable medical device of claim 8, wherein the housing comprises the plurality of electrodes.

17. A method comprising:
delivering therapeutic electrical stimulation from a medical device to a patient via a plurality of electrodes to inhibit delivery of therapeutic electrical stimulation to the patient by another implantable medical device; and
modulating the therapeutic electrical stimulation delivered by the medical device according to a predetermined pattern to provide a disable command to the other implantable medical device,
wherein the other implantable medical device is disabled in response to receipt of the disable command.

18. The method of claim 17, wherein delivering therapeutic electrical stimulation from a medical device and modulating the therapeutic electrical stimulation delivered by the medical device comprises delivering therapeutic electrical stimulation from an implantable medical device and modulating the therapeutic electrical stimulation delivered by the implantable medical device.

19. The method of claim 17, wherein the medical devices comprise cardiac pacemakers, and the therapeutic electrical stimulation comprises cardiac pacing.

20. The method of claim 17,
wherein the therapeutic electrical stimulation comprises pulses,
the method further comprising determining, by the medical device, a rate of delivery of the pulses by the other implantable medical device,
wherein delivering therapeutic electrical stimulation from the medical device to inhibit delivery of therapeutic electrical stimulation to the patient by another implantable medical device comprises delivering, by the medical devices, pulses at a greater rate to inhibit the delivery of pulses by the other implantable medical device.

21. The method of claim 17, wherein the therapeutic electrical stimulation comprises pulses, and modulating the therapeutic electrical stimulation according to a predetermined pattern to provide a disable command comprises modulating a length of intervals between consecutive ones of the pulses to provide the disable command.

22. The method of claim 17, wherein the therapeutic electrical stimulation comprises pulses, and modulating the therapeutic electrical stimulation according to a predetermined pattern to provide a disable command comprises modulating at least one of an amplitude, frequency, or width of the therapeutic electrical stimulation to provide the disable command.

23. A method for disabling a first medical device previously implanted within a patient with a second implanted medical device more recently implanted in the patient, the method comprising:
controlling a therapy delivery module of the more recently implanted medical device to deliver a signal to the patient via at least one electrode that is coupled to the more recently implanted medical device and implanted within the patient;
modulating the signal by the more recently implanted medical device to provide a disable command to the previously implanted medical device;
detecting the signal by the previously implanted medical device via at least one electrode that is coupled to the previously implanted medical device and implanted within the patient and a sensing module of the previously implanted medical device that is configured to detect intrinsic electrical activity of the patient via the electrode; and
identifying, by the previously implanted medical device, the disable command within the detected signal,
wherein the previously implanted medical device is disabled in response to receipt of the disable command.

24. The method of claim 23, wherein controlling the therapy delivery module of the more recently implanted medical device to deliver the signal to the patient comprises controlling the therapy delivery module of the more recently implanted medical device to deliver the signal during a refractory period of tissue of the patient.

25. The method of claim 23, wherein the previously implanted medical device and the more recently implanted medical device comprise leadless pacemakers.

26. The method of claim 23, wherein the more recently implanted medical device replaces the previously implanted medical device.

* * * * *